United States Patent [19]

Sogah

[11] 4,448,980

[45] May 15, 1984

[54] PREPARATION OF TRIALKYLSILYL ETHERS

[75] Inventor: Dotsevi Y. Sogah, Wilmington, Del.

[73] Assignee: E. I. Du Pont de Nemours and Company, Wilmington, Del.

[21] Appl. No.: 534,778

[22] Filed: Sep. 22, 1983

[51] Int. Cl.$^3$ .................. C07F 7/18; C07F 7/08; C07F 7/10

[52] U.S. Cl. .................. 556/446; 556/436; 556/438; 556/470; 556/417; 556/405; 260/349

[58] Field of Search .............. 556/446, 436, 438, 417, 556/405, 470; 260/349

[56] References Cited

U.S. PATENT DOCUMENTS

| | | | |
|---|---|---|---|
| 3,637,630 | 1/1972 | Dorfmann et al. | 260/88.7 E |
| 3,917,542 | 11/1975 | Beschke et al. | 252/442 |
| 4,017,518 | 4/1977 | Gorbunov et al. | 260/340.7 |
| 4,266,064 | 5/1981 | Nishiyama et al. | 546/345 |
| 4,332,654 | 6/1982 | Yates | 556/470 X |
| 4,377,706 | 3/1983 | Hallgren | 556/470 X |
| 4,414,372 | 11/1983 | Farnham et al. | 526/190 |
| 4,417,034 | 11/1983 | Webster | 526/190 |

OTHER PUBLICATIONS

Rasmussin, "O-Silylated Enolates-Versatile Intermediates for Organic Synthesis", Synthesis, 91 (1977), pp. 91–96.
Dunogues, Chemtech (6), 373 (Jun. 1982).
Mukaiyama et al., J. Am. Chem. Soc. 96, 7503 (1974).
Saigo et al., Chem. Letters, 163 (1976).
Nakamura et al., J. Am. Chem. Soc. 98, 2346 (1976).
Noyori et al., and Kuwajima et al., J. Am. Chem. Soc. 99, 1265 (1977).
Kuwajima et al., J. Am. Chem. Soc. 104, 1025 (1982).
Noyori et al., Tetrahedron Letters 21, 2085 (1980).
Clark, Chem. Rev. 80, 429 (1980).
Colvin, "Silicon in Organic Chemistry", Butterworths, London (1981) pp. 219, 220 and 227.
Kita et al., Synthesis Comm., 1089 (1982).
Gostevskii et al., J. Organometallic Chem. 187, 157 (1980).
Delyagina et al., Izv. Akad. Nauk SSSR, Ser. Khim., No. 10, 2238 (1981).
Nakamura et al., J. Org. Chem., 48, 932 (1983).
Sharma et al., J. Org. Chem., 48, 2112 (1983).

*Primary Examiner*—Paul F. Shaver

[57] ABSTRACT

In an improved catalytic process for preparing trialkylsilyl ethers from trialkylsilyl compounds and carbonyl group-containing compounds, the improvement consisting of using an organic or inorganic bifluoride (HF$_2^\ominus$) as the catalyst.

21 Claims, No Drawings

PREPARATION OF TRIALKYLSILYL ETHERS

BACKGROUND OF THE INVENTION

1. Technical Field

This invention relates to the catalyzed preparation of trialkylsilyl ethers.

2. Technical Background

The trialkylsilyl ethers of this invention, as well as the trialkylsilyl and carbonyl compounds which are used to prepare the trialkylsilyl ethers of this invention, are well known in the art.

Rasmussin, "O-Silylated Enolates-Versatile Intermediates For Organic Synthesis", Synthesis, 91 (1977), especially pages 91–96, provides a review of silyl enol ethers and ketene silyl acetals, their preparation and reactions. The addition of allylsilanes to aldehydes and ketones in the presence of Lewis acids to form trialkylsilyl ethers is discussed by Dunoguès, Chemtech (6), 373 (June 1982). Cross-Aldol reactions of silyl enol ethers with carbonyl compounds, activated by titanium tetrachloride, can be carried out under mild conditions, according to Mukaiyama et al., J. Am. Chem. Soc. 96, 7503 (1974). In a related later paper, Chem. Letters, 163 (1976), Saigo et al. discuss the Michael-type reaction of O-silylated ketene acetals with $\alpha,\beta$-unsaturated carbonyl compounds, promoted by titanium tetrachloride. Nakamura et al., J. Am. Chem. Soc. 98, 2346 (1976) disclose the reaction of ethyl trimethylsilylacetate and tetra-n-butylammonium fluoride with various aromatic and alicyclic ketones and alcohols, and Noyori et al. and Kuwajima et al., J. Am. Chem. Soc. 99, 1265 (1977), describe fluoride ion catalyzed reactions of trimethylsiloxycyclohexenes and benzaldehyde. In J. Am. Chem. Soc. 104, 1025 (1982) Kuwajima et al. describe fluoride ion catalyzed reactions of trimethylsiloxyolefins and alkyl halides.

The alkylation of trimethylsiloxyolefins in the presence of tris(diethylamino)sulfonium difluorotrimethylsilicate as a fluoride ion source is discussed by Noyori et al. in Tetrahedron Letters 21, 2085 (1980). Clark, Chem. Rev. 80, 429 (1980), "Fluoride Ion as a Base in Organic Synthesis," discloses on page 441 aldol-type reactions of trimethylsiloxyolefins and aldehydes in the presence of a fluoride ion source, such as tetraalkylammonium fluoride.

Colvin, "Silicon in Organic Chemistry," Butterworths, London (1981), discloses on pages 219, 220 and 227 reactions of trimethylsiloxyolefins and aromatic aldehydes in the presence of tetra-n-butylammonium fluoride, and Kita et al., Synthesis Comm., 1089 (1982) disclose reactions of [(1-methoxy-1-propenyl)oxy]trimethylsilane and ketones in the presence of tetra-n-butylammonium fluoride. Gostevskii et al., J. Organometallic Chem. 187, 157 (1980), describe cyanide or fluoride ion catalyzed reactions of trialkylsilanes and carbonyl compounds to form trialkylsilyl ethers. Delyagina et al., Izv. Akad. Nauk SSSR, Ser. Khim., No. 10, 2238 (1981), English language translation, disclose that the bifluoride ion source $[(CH_3)_2N]_2CH^{\oplus}HF_2^{\ominus}$ adds more readily to fluoroolefins than conventional fluoride ion sources such as CsF or KF.

U.S. Pat. No. 3,637,630 discloses the use of fluorides and bifluorides as catalysts for preparing triazines from haloalkane nitriles and for cross-linking (curing) polymers containing cyanohaloalkyl groups. U.S. Pat. No. 3,917,542 discloses the use of ammonium hydrogen fluoride as a catalyst in the reaction of acrolein and ammonia to form pyridine and 3-methylpyridine. U.S. Pat. No. 4,017,518 discloses the use of acidic inorganic salts, including $KHF_2$, as catalysts for preparing 4,4-dimethyldioxane-1,3 by reacting isobutylene and formaldehyde in aqueous medium. U.S. Pat. No. 4,266,064 discloses the preparation of a chloro-$\beta$-trifluoromethylpyridine by reacting a chloro-$\beta$-trichloromethylpyridine and HF in the presence of a selected metal fluoride or mixture thereof with ammonium fluoride or ammonium acid fluoride ($NH_4F \cdot HF$). European Patent Application Publication No. 0 068 887, corresponding to U.S. patent application Ser. Nos. 389,110 and 389,111, discloses the polymerization of methacrylic and acrylic monomers, initiated by trialkylsilyl compounds and catalyzed by various nucleophilic anions, including fluoride and cyanide, selected Lewis acids, and bifluoride ions.

SUMMARY OF THE INVENTION

The trialkylsilyl and carbonyl compounds used in the process of this invention, their reaction in the presence of catalysts, and the trialkylsilyl ether products of the process are known in the art. The novel and unobvious feature of the invention process is the use of bifluoride ions as catalysts in the preparation of trialkylsilyl ethers. Sources of the bifluoride ion are also known compounds, but their use as catalysts for the preparation of trialkylsilyl ethers, or in any related reaction, is not known in the art. Publications describing the use of various catalysts, including fluoride and cyanide anions and Lewis acids, in the preparation of related alkylsilyl ethers have been disclosed above. With reference to the above, bifluoride and other anions, such as fluoride and cyanide, and selected Lewis acids, such as $ZnBr_2$, have been used as catalysts in the polymerization of methacrylic and acrylic monomers, the polymerization being initiated by trialkylsilyl compounds such as those used as reactants in the process of this invention. Bifluoride ion has also been shown to add to fluorinated olefins, as does fluoride ion. It has now been discovered that bifluorides are unusually more versatile catalysts for preparing a wider variety of silyl ethers than any other individual catalysts disclosed in the art.

It is believed to be surprising and unexpected that addition reactions of carbonyl compounds and trialkylsilyl compounds should be catalyzed so effectively by bifluoride ion. Known catalysts for these reactions are aprotic, strongly nucleophilic anions, such as fluoride and cyanide, or Lewis acids, such as titanium tetrachloride. In contrast, bifluoride ion F—H—F$^\ominus$ is protonic and has not been used or considered in the art as a nucleophilic agent, with the possible exception of fluoroolefin addition reactions (Delyagina et al., supra).

Cleavage of trimethylsiloxy (—$OSi(CH_3)_3$) groups to give hydroxyl (—OH) groups in the presence of protonic or Lewis acids or metal fluorides is known (for example, Dunoguès, supra).

DETAILED DESCRIPTION OF THE INVENTION

The invention herein provides a process for preparing trialkylsilyl ethers of the formula

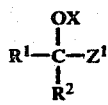

by mixing and reacting in the presence of bifluoride ion ($HF_2^{\ominus}$) the trialkylsilyl compound of the formula $(R)_3SiZ$ and the carbonyl compound having the formula

In the formulae:
X is $Si(R)_3$;
R is $C_{1-4}$ alkyl;
$R^1$ is $C_{1-10}$ alkyl or $C_{6-10}$ cycloalkyl, aryl, alkaryl or aralkyl;
$R^2$ is —H, —$R^1$ or —$OR^3$;
$R^1$ and $R^2$ taken together are $-(CH_2)_5$;

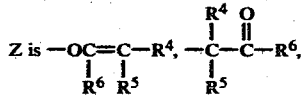

(a)

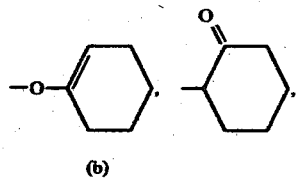

(b)

—H,   —CN,   —$N_3$,   —SR,   —$OP(OR^3)_2$, —$OP[N(R)_2]_2$,

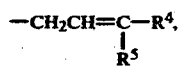

—$CH_2CN$ or —$C_6F_5$;
$Z^1$ is Z, provided, however, $Z^1$ is not (a) or (b);
$R^3$ is —$Si(R)_3$ or $C_{1-4}$ alkyl, optionally substituted with —$Si(R)_3$ or —$OSi(R)_3$;
$R^4$ and $R^5$ are independently selected from —H and $C_{1-4}$ alkyl;
$R^6$ is —H, $C_{1-6}$ alkyl, aryl or —$OR^7$; and
$R^7$ is —$Si(R)_3$ or $C_{1-4}$ alkyl, optionally substituted with —$Si(R)_3$ or —$OSi(R)_3$.

The process of the invention may be represented by the equation:

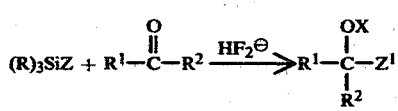

wherein R, $R^1$, $R^2$, X, Z and $Z^1$ are defined as above.

Preferred embodiments of the process of the invention include those wherein:

(1) the silyl ether product is hydrolyzed to an alcohol, that is, wherein —OX is hydrolyzed to —OH;

(2) the product wherein —OX is hydrolyzed in the presence of fluoride ion;

(3) Z is 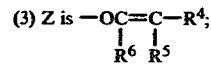

(4) Z is 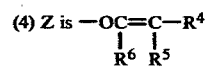

wherein each of $R^4$ and $R^5$ is independently selected from —H and —$CH_3$, $R^6$ is $C_{1-6}$ alkyl, phenyl or —$OR^7$, and $R^7$ is $C_{1-4}$ alkyl, —$Si(R)_3$ or —$CH_2CH_2OSi(R)_3$, and further, wherein $R^1$ is $C_{1-10}$ alkyl, cyclohexyl or phenyl, and $R^2$ is —H or —$CH_3$, and still further, wherein the catalyst is tris(dimethylamino)sulfonium bifluoride;

(5) Z is

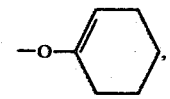

and further, wherein R is —$CH_3$, $R^1$ is phenyl and $R^2$ is —H.

In carrying out the process, a trialkylsilyl compound $(R)_3SiZ$ and a carbonyl compound $R^1C(O)R^2$ are combined, preferably in approximately equimolar quantities, in the presence of a catalytic amount of a bifluoride compound. A solvent is desirable but not essential. All ingredients should be freshly prepared and free from moisture and should preferably be mixed and reacted under an inert atmosphere, such as argon or nitrogen. The order of addition of the ingredients is not critical. It has been found convenient to mix together the silyl compound, the solvent and the catalyst, and then slowly add the carbonyl compound, with stirring, at a temperature of about −80° to 100° C. When all the ingredients are admixed, the reaction mixture is maintained at a temperature in the range of about 0° to about 80° C., preferably 15° to 40° C., until reaction is complete. Alternatively, one may add, continuously with stirring, a mixture of the silyl and the carbonyl compounds to a bifluoride catalyst-solvent mixture. Reaction time, which varies with ingredients, concentration and temperature, is normally in the range of a few minutes to several hours.

A significant feature of the process of this invention is that the reaction being effected in the process can be carried out at a much higher temperature than corresponding reactions carried out with catalysts of the art, for example, a fluoride catalyst. Whereas the corresponding fluoride ion catalyzed reactions of the art usually are carried out at about −80° C., and no higher than −50° C., the reaction of the instant invention with bifluoride catalyst is carried out at about 0° to about 80° C., preferably at 15° to 40° C., that is, at about room temperature or at slightly below or slightly above room temperature.

Suitable solvents include tetrahydrofuran, acetonitrile, nitromethane, toluene, xylenes, chlorobenzene, benzonitrile, glyme, diglyme and methyl tert-butyl ether. Tetrahydrofuran is preferred. Molar ratios of solvent to silyl compound in the range of about 1:1 to about 500:1 can be employed.

Suitable sources of bifluoride ion catalyst include both organic and inorganic bifluorides, providing such compounds are at least partly soluble in the solvent employed. Preferred organic bifluorides are tris(dialkylamino)sulfonium bifluorides wherein each alkyl contains 1 to 20 carbon atoms; most preferred is tris(dimethylamino)sulfonium bifluoride, the preparation of which is described in Example 1A. Suitable inorganic bifluorides include the alkali metal, ammonium and quaternary ammonium bifluorides. Potassium bifluoride is a preferred inorganic bifluoride because of its lower cost.

The bifluoride catalyst should be present in a catalyst-:silyl compound molar ratio of about 0.001:1 to about 0.1:1, preferably about 0.005:1 to 0.05:1.

Reaction pressure is not critical and the reaction can be carried out at such pressure as is convenient or feasible in the equipment or apparatus which is available. For example, the reaction can be carried out at subatmospheric, atmospheric or superatmospheric pressure. It usually is most convenient to carry out the reaction at atmospheric pressure and, for this reason, atmospheric pressure is preferred.

When reaction is complete, conventional product isolation methods are employed. For example, the reaction mixture can be treated with a lower alkanol, such as methanol, and the solvent-methanol mixture evaporated under reduced pressure. The residue contains the products as liquids or solids, which are freed from residual solvent and alkanol by heating at about 30° to 60° C. under vacuum, and from catalyst residues by extraction with water.

The trialkylsilyl ether product can be converted, by treatment with an aqueous mineral acid or other known reagent, such as a source of fluoride ion, either to the corresponding alcohol wherein the —OSi(R)$_3$ group is replaced with an —OH group, or, in certain cases, to internal olefins by elimination of HOSi(R)$_3$. Treatment with an alkali metal fluoride is preferred. The final product is a functional organic compound which is useful as an intermediate in chemical synthesis.

The following examples illustrate the invention. A key to the reactants and products of these examples is given in Table 1. The symbols therein are as defined above except where otherwise indicated. Parts are by weight unless otherwise indicated, and temperatures are in degrees Celsius.

TABLE 1

R is CH$_3$ in every example.
Catalyst is (TAS)HF$_2$ (See Example 1).

| Ex. | R$^1$ | R$^2$ | R$^3$ | Z | Z$^1$ | R$^4$ | R$^5$ | R$^6$ | R$^7$ |
|---|---|---|---|---|---|---|---|---|---|
| 1 | (CH$_3$)$_2$CH | H | — | a | c | CH$_3$ | CH$_3$ | OR$^7$ | CH$_3$ |
| 2 | (CH$_3$)$_2$CH | H | — | a | c | H | CH$_3$ | OR$^7$ | CH$_3$ |
| 3 | C$_6$H$_5$ | H | — | a | c | CH$_3$ | CH$_3$ | OR$^7$ | CH$_3$ |
| 4 | C$_6$H$_5$ | H | — | a | c | H | H | OR$^7$ | (CH$_3$)$_3$C |
| 5 | C$_6$H$_5$ | H | — | a | c | H | CH$_3$ | OR$^7$ | CH$_3$ |
| 6 | C$_6$H$_5$ | H | — | a | c | CH$_3$ | CH$_3$ | OR$^7$ | Si(R)$_3$ |
| 7 | C$_6$H$_5$ | H | — | a | c | CH$_3$ | CH$_3$ | OR$^7$ | CH$_2$CH$_2$OSi(R)$_3$ |
| 8 | C$_6$H$_5$ | CH$_3$ | — | a | c | CH$_3$ | CH$_3$ | OR$^7$ | CH$_3$ |
| 9 | ƒCH$_2$)$_5$ | — | — | a | c | CH$_3$ | CH$_3$ | OR$^7$ | CH$_3$ |
| 10 | CH$_3$ | H | — | a | c | CH$_3$ | CH$_3$ | OR$^7$ | CH$_3$ |
| 11 | (CH$_3$)$_2$CHCH$_2$ | CH$_3$ | — | a | c | CH$_3$ | CH$_3$ | OR$^7$ | CH$_3$ |
| 12 | C$_6$H$_5$ | H | — | b | d | — | — | — | — |
| 13 | ƒCH$_2$)$_5$ | — | — | a | c | H | H | C$_6$H$_5$ | — |
| 14 | C$_6$H$_5$ | H | — | a | c | H | H | C$_6$H$_5$ | — | a: 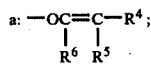

b: 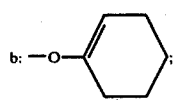

c: 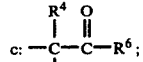

d: 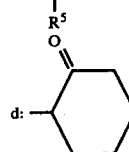

EXAMPLE 1

A. Preparation of Tris(dimethylamino)sulfonium bifluoride [(CH$_3$)$_2$N]$_3$SHF$_2$ Tris(dimethylamino)sulfonium difluorotrimethylsilicate (11.22 g, 40.7 mmol) was dissolved in 10 mL of distilled acetonitrile under argon and 0.6 mL (33 mmol) of water was added. An oily material formed rapidly. The solvent and water were evaporated and the recovered solid product was stirred overnight in 100 mL of tetrahydrofuran. A crystalline product was obtained which, after filtration under argon and drying at 25° at 0.1 mm Hg for 3 days, weighed 8.20 g (99.7% yield). $^{19}$F NMR and elemental analysis confirmed the structure [(CH$_3$)$_2$N]$_3$SHF$_2$, commonly referred to as (TAS)HF$_2$. $^{19}$F NMR (CD$_3$CN, 0°): δ −145.8 (doublet, $J_{HF}$=120 Hz). Anal. calcd. for C$_6$H$_{19}$F$_2$N$_3$S: C 35.47, H 9.42, F 18.68, N 20.66, S 15.77. Found: C 35.45, H 9.36, F 17.52, N 20.99, S 16.15.

B. Preparation of Tris(dimethylamino)sulfonium bifluoride [(CH$_3$)$_2$N]$_3$SHF$_2$ In another preparation of tris(dimethylamino)sulfonium bifluoride, the above procedure was followed using 27.5 g (100 mmol) of the starting silicate and 1.0 mL (55 mmol) of water. However, the solid product obtained after evaporation of solvent and water was not treated with tetrahydrofuran. Yield was quantitative and $^{19}F$ NMR and elemental analysis confirmed the above bifluoride structure.

C. Reaction of [(1-Methoxy-2-methyl-1-propenyl)oxy]trimethylsilane and Isobutyraldehyde To a stirred suspension of $(TAS)HF_2$ (20 mg, 0.1 mmol) in tetrahydrofuran (10 mL) under argon was added [1-methoxy-2-methyl-1-propenyl)oxy]trimethylsilane (1.74 g, 10 mmol) at 20°. Then, freshly distilled isobutyraldehyde (0.72 g, 10 mmol) was added dropwise. The mixture was stirred for 1 h and then treated with methanol (5 mL). The solvent and methanol were evaporated at reduced pressure and the residue was dried at 40°/0.1 mm Hg for 2 h to give 2.20 g of methyl 2,2,4-trimethyl-3-trimethylsiloxyvalerate (89% yield). NMR (CDCl$_3$, ppm): 3.75 (CH, d); 3.62 (CH$_3$O, s); 1.40–2.01 (CH, m); 1.10 (CH$_3$, d); 0.80 (CH$_3$, d of d); 0.14 (CH$_2$Si, s).

D. Reaction of [(1-Methoxy-2-methyl-1-propenyl)oxy]trimethylsilane and Isobutyraldehyde In another preparation of the aforesaid valerate, isobutyraldehyde (0.72 g) was added to a mixture of [(1-methoxy-2-methyl-1-propenyl)oxy]trimethylsilane (1.74 g, 10 mmol) and $(TAS)HF_2$ (100 mg, 0.1 mmol) in 20 mL of tetrahydrofuran under argon at −11°. The reaction mixture was stirred and the temperature was allowed to rise to 23°. Stirring was continued for 18 h and the mixture was then poured into 200 mL of ethyl acetate and extracted with water (200 mL), followed by washing with aqueous brine (200 mL). The organic layer was dried (MgSO$_4$), filtered and evaporated in vacuo to give 2.39 g (97% yield) of methyl 2,2,4-trimethyl-3-trimethylsiloxyvalerate.

E. Cleavage of the Trimethylsilyl Group of Methyl 2,2,4-trimethyl-3-trimethylsiloxyvalerate The 2.20 g of product from Part C was dissolved in 100 mL of dichloromethane, treated with 100 mL of 0.5 M hydrochloric acid, and then washed with aqueous brine (100 mL). The organic layer was dried (MgSO$_4$), filtered and evaporated to give methyl 2,2,4-trimethyl-3-hydroxyvalerate (98% yield). NMR (CDCl$_3$, ppm); 3.65 (CH$_3$O, s); 3.40 (CH, d); 2.90 (OH, broad s); 1.50–2.10 (CH, m); 1.25 (CH$_3$, d); 0.90 (CH$_3$, d of d).

In the products of Parts C, D and E there are asymmetric carbon atoms. Hence, groups attached to them are diastereotopic and appear as doublets or sets of doublets in the NMR.

EXAMPLE 2

Reaction of [(1-Methoxy-1-propenyl)oxy]trimethylsilane and Isobutyraldehyde and In-situ Cleavage of the Trimethylsilyl Group Using the procedure of Example 1C, [(1-methoxy-1-propenyl)oxy]trimethylsilane (3.2 g, 20 mmol) and isobutyraldehyde (1.44 g, 20 mmol) were reacted in the presence of $(TAS)HF_2$ (41 mg, 0.20 mmol) and 10 mL of tetrahydrofuran to form methyl 2,4-dimethyl-3-trimethylsiloxyvalerate. Without isolating the valerate, the reaction mixture was stirred another 1 h and then treated with KF (5.6 g) in methanol (20 mL). The resulting mixture was refluxed for 3 h, cooled and then evaporated. The residue was dissolved in 100 mL of dichloromethane, washed with water (100 mL) and then with aqueous brine (100 mL). The organic layer was dried (MgSO$_4$), filtered and evaporated to give 2.7 g (84% yield) of methyl 2,4-dimethyl-3-hydroxyvalerate (mixture of diastereomers).

EXAMPLE 3

A. Reaction of [(1-Methoxy-2-methyl-1-propenyl)oxy]trimethylsilane and Benzaldehyde A solution of a mixture of freshly distilled benzaldehyde (1.08 g, 10 mmol) and [(1-methoxy-2-methyl-1-propenyl)oxy]trimethylsilane (1.74 g, 10 mmol) in 5 mL of tetrahydrofuran was added dropwise under argon to a suspension of $(TAS)HF_2$ (100 mg, 0.50 mmol) in tetrahydrofuran. The mixture was stirred at ambient temperature for 15 h, to produce methyl 2,2-dimethyl-3-phenyl-3-trimethylsiloxypropionate, and then treated in-situ with methanol/conc. HCl (10/2 v/v). The colorless solution was stirred for 15 minutes and evaporated. The residue was dissolved in dichloromethane (200 mL) and extracted successively with 0.1 M HCl (100 mL) and aqueous brine (100 mL). The organic layer was dried (MgSo$_4$) filtered and evaporated to give 1.60 g of methyl 2,2-dimethyl-3-hydroxy-3-phenylpropionate (dried at 40°/0.1 mm Hg) as an oil. NMR (CDCl$_3$, ppm): 1.03 (CH$_3$, 6H, d); 3.58 (CH$_3$O, 3H, s); 3.50 (OH, 1H, s); 4.83 (ArCH, 1H, s); 7.23 (ArH, 5H).

B. Reaction of [(1-Methoxy-2-methyl-1-propenyl)oxy]trimethylsilane and Benzaldehyde The bifluoride-catalyzed reaction of [(1-methoxy-2-methyl-1-propenyl)oxy]trimethylsilane and benzaldehyde was run at a lower temperature than in Part A, as follows: To a stirred suspension of $(TAS)HF_2$ (20 mg, 0.1 mmol) in tetrahydrofuran (20 mL) under argon was added [(1-methoxy-2-methyl-1-propenyl)oxy]trimethylsilane (1.74 g) at 23°. The mixture was cooled to 0° and a solution of benzaldehyde (1.04 g) in tetrahydrofuran (5 mL) was added via a syringe pump over 20 minutes. The mixture was stirred for 2 h while the temperature was maintained between −3° and 1°. The clear colorless mixture was evaporated at reduced pressure and the residue was dried at 40°/0.3 mm Hg to give 2.58 g (94% yield) of methyl 2,2-dimethyl-3-phenyl-3-trimethylsiloxypropionate. NMR (CDCl$_3$, ppm): −0.12 (CH$_3$Si, s); 0.98 (CH$_3$, d); 3.58 (CH$_3$O, s); 4.90 (ArCH, s); 7.20 (ArH, m).

EXAMPLE 4

Reaction of t-Butyl 2-Trimethylsilylacetate and Benzaldehyde

To a reaction vessel containing $(TAS)HF_2$ (100 mg, 0.5 mmol) was slowly added, under argon and with stirring, a mixture of tetrahydrofuran (3 mL), benzaldehyde (1.06 g, 10 mmol) and t-butyl 2-trimethylsilylacetate. The temperature rose from 22° to 41° during the addition. Stirring was continued for 15 h, after which a sample was found by chromatography to contain no residual aldehyde. Methanol (10 mL) and conc. HCl (2 mL) were added and the mixture was stirred for 15 minutes and evaporated. The residue was dissolved in methylene chloride (200 mL), washed with 0.1 M HCl (100 mL), washed with aqueous brine (100 mL), and then dried (MgSO$_4$), filtered, evaporated and redried. A white crystalline residue (0.81 g) was identified by NMR and IR as a mixture of the methyl and tert-butyl esters of cinnamic acid.

EXAMPLE 5
Reaction of [(1-Methoxy-1-propenyl)oxy]trimethylsilane and Benzaldehyde To a stirred suspension of (TAS)HF$_2$ (100 mg, 0.5 mmol) in tetrahydrofuran (5 mL) under argon was added a mixture of benzaldehyde (1.04 g, 10 mmol) and [(1-methoxy-1-propenyl)oxy]trimethylsilane (1.60 g, 10 mmol) in tetrahydrofuran (5 mL). The mixture was stirred at ambient temperature for 15 h, to give methyl 2-methyl-3-phenyl-3-trimethylsiloxypropionate, and then treated in-situ with 10 mL of methanol containing 2 mL of conc. HCl. After being stirred for 15 minutes the mixture was evaporated and the residue was dissolved in 200 mL of dichloromethane. This was successively washed with 0.1 M HCl (100 mL) and aqueous brine (100 mL) and the dichloromethane layer was dried (MgSO$_4$), filtered and evaporated to give 1.4 g (74% yield) of methyl 2-methyl-3-hydroxy-3-phenylpropionate, obtained as a mixture of threo and erythro isomers. NMR (threo, CDCl$_3$, ppm): 7.17 (ArH, 5H); 4.88 (ArCH—O, 1H, d, J=5.3 Hz); 3.43 (CH$_3$O, 3H, s); 3.50 (OH, 1H, s); 2.40–2.87 (—CH—, 1H, m); 0.97 (CH$_3$, 3H, d, J=8.0 Hz). NMR (erythro, CDCl$_3$, ppm): 7.17 (ArH, 5H); 4.57 (ArCH—O, 1H, d, J=9.3 Hz); 3.52 (CH$_3$O, 3H, s); 3.50 (OH, 1H, s); 2.40–2.87 (—CH—, 1H, m); 0.77 (CH$_3$, 3H, d, J=8.0 Hz).

EXAMPLE 6
Reaction of [(2-Methyl-1-propenylidene)bis(oxy)]bis[trimethylsilane] and Benzaldehyde The procedure of Example 5, including the hydrolysis step, was repeated using [(2-methyl-1-propenylidene)bis(oxy)]bis[trimethylsilane] (1.85 g, 8.0 mmol) instead of [(1-methoxy-1-propenyl)oxy]trimethylsilane and 8 mmol instead of 10 mmol of benzaldehyde; 1.34 g(75.3% yield) of product, 2,2-dimethyl-3-hydroxy-3-phenylpropionic acid, was obtained. In this example the hydrolysis step not only removed the trimethylsilyl group but also converted the ester group to the free acid.

EXAMPLE 7
Reaction of [(1-[2-Trimethylsiloxyethoxy]-2-methyl-1-propenyl)oxy]trimethylsilane and Benzaldehyde

[(1-[2-Trimethylsiloxyethoxy]-2-methyl-1-propenyl)oxy]trimethylsilane (1.38 g, 5 mmol), benzaldehyde (0.53 g, 5 mmol) and (TAS)HF$_2$ (50 mg, 0.25 mmol) were mixed as described in Example 5, and the mixture was stirred at room temperature for 18 h. Solvent was then removed by evaporation and a sample of the residue was removed for analysis. The remaining residue was dissolved in methylene chloride (200 mL) and washed successively with 1 M HCl (200 mL) and aqueous brine (200 mL). The organic layer was dried, filtered and evaporated to give 1.46 g (94% yield) of viscous oil. Samples analyzed by NMR before and after acid hydrolysis were found to be, respectively, 2-trimethylsiloxyethyl 2,2-dimethyl-3-phenyl-3-trimethylsiloxypropionate and 2-trimethylsiloxyethyl 2,2-dimethyl-3-hydroxy-3-phenylpropionate. The trimethylsilyl group remaining in the latter compound after acid hydrolysis can be removed by known methods using fluoride ion catalysts, such as potassium fluoride or tetrabutylammonium fluoride, to form 2-hydroxyethyl 2,2-dimethyl-3-hydroxy-3-phenylpropionate.

EXAMPLE 8
A. Reaction of [(1-Methoxy-2-methyl-1-propenyl)oxy]trimethylsilane and Acetophenone To a stirred mixture of (TAS)HF$_2$ (100 mg, 0.50 mmol), [(1-methoxy-2-methyl-1-propenyl)oxy]trimethylsilane (1.74 g, 10 mmol) and tetraydrofuran (10 mL) was added acetophenone (1.2 g, 10 mmol) under argon at 22°. The reaction mixture was stirred for 18 h and then treated with methanol (5 mL). The solvent and methanol were evaporated off at reduced pressure. The residue, weighing 1.89 g, was identified by NMR to be mainly methyl 2,2-dimethyl-3-phenyl-3-trimethylsiloxybutyrate. NMR (CDCl$_3$, ppm): 7.30–7.40 (ArH, m); 3.56 (CH$_3$O, s); 1.70 (CH$_3$, s); 1.29 (CH$_3$, d); 0.10 (CH$_3$Si, s).

B.& C. Reaction of [(1-Methoxy-2-methyl-1-propenyl)oxy]trimethylsilane and Acetophenone The above reaction was repeated twice, except that the reactants were mixed at 0° and then (a) stirred for 18 h at 23°; (b) stirred 30 minutes at −50°. NMR analyses showed that the product in each case was mainly methyl 2,2-dimethyl-3-phenyl-3-trimethylsiloxybutyrate.

D. Reaction of [(1-Methoxy-2-methyl-1-propenyl)oxy[trimethylsilane and Acetophenone In a further experiment, [(1-methoxy-2-methyl-1-propenyl)oxy]trimethylsilane (1.74 g, 10 mmol) was added to a stirred suspension of (TAS)HF$_2$ (20 mg, 0.1 mmol) in tetrahydrofuran (20 mL) under argon. The resulting mixture was cooled to −3.2° and acetophenone (1.20 g, 10 mmol) dissolved in 5 mL of tetrahydrofuran was added via a syringe pump over a 1 h period. The reaction mixture was stirred at −3.2° to 0.4° for 2 h. The solvent was evaporated and the products were dried at 40°–45°/1.0 mm Hg (2.25 g recovered). NMR analyses showed a mixture of products, including 54% methyl 2,2-dimethyl-3-phenyl-3-trimethylsiloxybutyrate, 31% [(1-phenylethenyl)oxy]trimethylsilane and 5% acetophenone.

E. Cleavage of the Trimethylsilyl Group of Methyl 2,2-dimethyl-3-phenyl-3-trimethylsiloxybutyrate The 1.89 g residue from Part A was dissolved in dichloromethane (200 mL) and washed successively with 0.1 M HCl (100 mL) and aqueous brine (100 mL). The organic layer was dried (MgSO$_4$), filtered and evaporated to give 1.59 g of methyl 2,2-dimethyl-3-hydroxy-3-phenylbutyrate. NMR (CDCl$_3$, ppm); 7.30–7.41 (ArH, m); 3.57 (CH$_3$O, s); 4.30 (OH, s); 1.60 (CH$_3$, s); 1.10 (CH$_3$, s).

EXAMPLE 9

Reaction of [(1-Methoxy-2-methyl-1-propenyl)oxy]trimethylsilane and Cyclohexanone To a stirred suspension of (TAS)HF$_2$ (20 mg, 0.1 mmol) in tetrahydrofuran (20 mL) at 22° was added [(1-methoxy-2-methyl-1-propenyl)oxy]trimethylsilane (1.74 g, 10 mmol). The resulting mixture was cooled to about 0° and a solution of cyclohexanone (0.98 g, 10 mmol) in tetrahydrofuran (10 mL) was added via a syringe pump over a 20 minute interval. The reaction mixture was stirred for 2 h, the temperature being maintained between −3.8° and −0.2°. The solvent was evaporated off at reduced pressure and the residue was dried at 40°/1.0 mm Hg to give 2.32 g (85% yield) of methyl 2-cyclohexyl-2-methyl-2-trimethylsiloxypropionate. NMR (CDCl$_3$, ppm): 3.66 (OCH$_3$, s); 1.28–2.13 (CH$_2$, 10H, m); 1.21 (CH$_3$, s); 0.20 (CH$_3$Si, s).

EXAMPLE 10

Reaction of [(1-Methoxy-2-methyl-1-propenyl)oxy]trimethylsilane and Acetaldehyde (TAS)HF$_2$ (0.1 mL of a 1 M solution in acetonitrile) was added to 20 mL of tetrahydrofuran. The solution was cooled to 0° and [(1-methoxy-2-methyl-1-propenyl)oxy]trimethylsilane (1.74 g, 10 mmol) was added. The mixture was cooled to −11° and acetaldehyde (0.44 g, 10 mmol) in 5 mL of tetrahydrofuran was added. Exothermic reaction occurred. The solution temperature was restored to −10° and stirred for 2 h. Evaporation gave 0.73 g of product which was shown by NMR analysis to be methyl 2,2-dimethyl-3-trimethylsiloxybutyrate.

EXAMPLE 11

Reaction of [(1-Methoxy-2-methyl-1-propenyl)oxy]trimethylsilane and Methyl Isobutyl Ketone Substitution of methyl isobutyl ketone (1.0 g, 10 mmol) for acetaldehyde in Example 10 gave 0.13 g of product which was shown by NMR analysis to be methyl 2,2,3,5-tetramethyl-3-trimethylsiloxyhexanoate.

EXAMPLE 12

Reaction of (1-Cyclohexenyl)oxytrimethylsilane and Benzaldehyde

To a stirred suspension of (TAS)HF$_2$ (20 mg, 0.1 mmol) in tetrahydrofuran (10 mL) cooled to −10° was added (1-cyclohexenyl)oxytrimethylsilane (1.92 g, 10 mmol), followed by a solution of benzaldehyde (1.0 mL) in tetrahydrofuran (10 mL); the aldehyde was added slowly from a syringe pump over a 30 minute interval. The reaction mixture was stirred at −10° for 1 h. Solvent was evaporated under reduced pressure and 1.34 g of a glassy product was obtained, shown by NMR to be 2-(phenyltrimethylsiloxymethyl)cyclohexanone.

EXAMPLE 13

Reaction of [(1-Phenylethenyl)oxy]trimethylsilane and Cyclohexanone

The procedure of Example 12 was followed using [(1-phenylethenyl)oxy]trimethylsilane (1.92 g, 10 mmol) and cyclohexanone (1.04 mL in 10 mL of tetrahydrofuran). The product (0.58 g) was shown by NMR to be 2-(1-trimethylsiloxycyclohexyl)acetophenone.

EXAMPLE 14

Substitution of benzaldehyde (1.0 mL in 10 mL of tetrahydrofuran) for cyclohexanone in Example 13 gave 1.83 g of a viscous oil which was shown by NMR to be (3-phenyl-3-trimethylsiloxy)propiophenone.

BEST MODE FOR CARRYING OUT THE INVENTION

The best mode for carrying out the invention is illustrated by Examples 1A, 1D, 2, 3B, 5, 6 and 8D.

INDUSTRIAL APPLICABILITY

Compounds which can be prepared through the use of the process of this invention include trialkylsilyl ethers, alcohols, esters, aldehydes, ketones, or combinations thereof, which have broad utility as chemical synthesis intermediates, for example, in the preparation of pharmaceutical products.

Although the preferred embodiments of the invention have been illustrated and described herein, it is to be understood that there is no intent to limit the invention to the precise constructions herein disclosed and it is to be further understood that the right is reserved to all changes and modifications coming within the scope of the invention as defined in the appended claims.

I claim:

1. Process comprising contacting and reacting (R)$_3$SiZ and R$^1$—C(O)—R$^2$ wherein R is C$_{1-4}$ alkyl;

R$^1$ is C$_{1-10}$ alkyl or C$_{6-10}$ cycloalkyl, aryl, alkaryl or aralkyl;

R$^2$ is —H, C$_{1-10}$ alkyl or C$_{6-10}$ cycloalkyl, aryl, alkaryl, aralkyl or —OR$^3$;

R$^3$ is —Si(R)$_3$ or C$_{1-4}$ alkyl, optionally substituted with —Si(R)$_3$ or —OSi(R)$_3$;

R$^1$ and R$^2$ taken together are $(CH_2)_5$; and

Z is 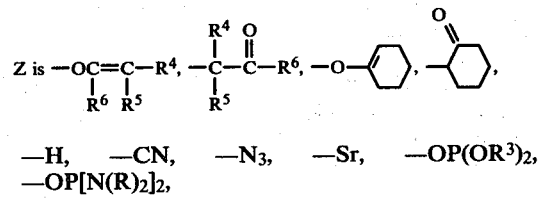

—H, —CN, —N$_3$, —Sr, —OP(OR$^3$)$_2$, —OP[N(R)$_2$]$_2$,

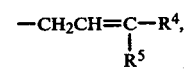

—CH$_2$CN or —C$_6$F$_5$;

R$^4$ and R$^5$ are independently selected from —H and C$_{1-4}$ alkyl;

R$^6$ is —H, C$_{1-6}$ alkyl, aryl or —OR$^7$; and

R$^7$ is —Si(R)$_3$ or C$_{1-4}$ alkyl, optionally substituted with —Si(R)$_3$ or —OSi(R)$_3$, in the presence of a catalytic amount of bifluoride (HF$_2^\ominus$) catalyst to produce the trialkylsilyl ether

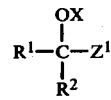

wherein

X is —Si(R)$_3$;

R, R$^1$ and R$^2$ are as defined above; and

Z$^1$ is 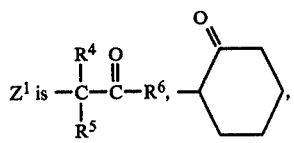

—H, —CN, —N$_3$, —SR, —OP(OR$^3$)$_2$, —OP[N(R)$_2$]$_2$,

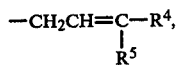

—CH$_2$CN or —C$_6$F$_5$.

2. Process of claim 1 wherein the molar ratio of HF$_2^\ominus$ to (R)$_3$SiZ is 0.001–0.1:1.0.

3. Process of claim 1 wherein the molar ratio of HF$_2^\ominus$ to (R)$_3$SiZ is 0.005–0.5:1.0.

4. Process of claim 1 wherein the bifluoride catalyst is selected from tris(dialkylamino)sulfonium bifluorides, wherein each alkyl contains 1 to 20 carbon atoms, and alkali metal, ammonium and quaternary ammonium bifluorides.

5. Process of claim 4 wherein the bifluoride catalyst is tris(dimethylamino)sulfonium bifluoride.

6. Process of claim 1 wherein (R)$_3$SiZ, R$^1$—C(O)—R$^2$ and the bifluoride catalyst are admixed at −80° to 100° C. and thereafter the process is carried out at 0° to 80° C.

7. Process of claim 6 wherein the process is carried out at 15° to 40° C.

8. Process of claim 1 wherein (R)$_3$SiZ and R$^1$—C(O)—R$^2$ are contacted in approximately equimolar quantities.

9. Process of claim 1 carried out in the presence of a solvent.

10. Process of claim 9 wherein the molar ratio of solvent to (R)$_3$SiZ is 1–500:1.

11. Process of claim 9 wherein the solvent is selected from tetrahydrofuran, acetonitrile, nitromethane, toluene, xylene, chlorobenzene, benzonitrile, glyme, diglyme and methyl tert-butyl ether.

12. Process of claim 9 wherein the solvent is tetrahydrofuran.

13. Process of claim 1 carried out at about atmospheric pressure.

14. Process of claim 1 comprising the further step of hydrolyzing the silyl ether product to an alcohol.

15. Process of claim 14 wherein said hydrolysis is carried out in the presence of fluoride ion.

16. Process of claim 1 wherein Z is

17. Process of claim 16 wherein R$^4$ and R$^5$, independently, are —H or —CH$_3$, R$^6$ is C$_{1-6}$ alkyl, phenyl or —OR$^7$ and R$^7$ is C$_{1-4}$ alkyl, —Si(R)$_3$, or —CH$_2$CH$_2$OSi(R)$_3$.

18. Process of claim 17 wherein R$^1$ is C$_{1-10}$ alkyl, cyclohexyl or phenyl and R$^2$ is —H or —CH$_3$.

19. Process of claim 18 wherein the catalyst is tris(dimethylamino)sulfonium bifluoride.

20. Process of claim 1 wherein Z is

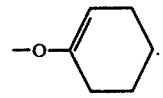

21. process of claim 20 wherein R is —CH$_3$, R$^1$ is phenyl and R$^2$ is —H.

* * * * *

UNITED STATES PATENT AND TRADEMARK OFFICE
CERTIFICATE OF CORRECTION

PATENT NO. : 4,448,980
DATED : May 15, 1984
INVENTOR(S) : Dotsevi Yao Sogah

It is certified that error appears in the above—identified patent and that said Letters Patent is hereby corrected as shown below:

Column 8, line 26, "MgSo$_4$" should read --MgSO$_4$--.

Column 10, line 16, "tetraydrofuran" should read --tetrahydrofuran--.

Column 12, line 47, "-Sr" should read -- -SR --.

Column 13, line 23, "0.005-0.5" should read --0.005-0.05--.

Signed and Sealed this

Twelfth Day of March 1985

[SEAL]

Attest:

DONALD J. QUIGG

Attesting Officer    Acting Commissioner of Patents and Trademarks